United States Patent
Son et al.

(10) Patent No.: US 12,133,994 B2
(45) Date of Patent: Nov. 5, 2024

(54) FOCUSED ULTRASOUND DEVICE AND IMAGE TRANSDUCER PROTECTION METHOD

(71) Applicant: IMGT CO., LTD., Seongnam-si (KR)

(72) Inventors: Keon Ho Son, Seongnam-si (KR); Dae Seung Kim, Seoul (KR); Ja Woon Koo, Gimpo-si (KR)

(73) Assignee: IMGT CO., LTD., Seongnam-si (KR)

( * ) Notice: Subject to any disclaimer, the term of this patent is extended or adjusted under 35 U.S.C. 154(b) by 0 days.

(21) Appl. No.: 18/262,632

(22) PCT Filed: Dec. 2, 2022

(86) PCT No.: PCT/KR2022/019445
§ 371 (c)(1),
(2) Date: Jul. 24, 2023

(87) PCT Pub. No.: WO2023/106740
PCT Pub. Date: Jun. 15, 2023

(65) Prior Publication Data
US 2024/0075322 A1 Mar. 7, 2024

(30) Foreign Application Priority Data
Dec. 8, 2021 (KR) .................. 10-2021-0175227

(51) Int. Cl.
*A61N 7/02* (2006.01)
*A61N 7/00* (2006.01)

(52) U.S. Cl.
CPC .......... *A61N 7/02* (2013.01); *A61N 2007/0052* (2013.01); *A61N 2007/0082* (2013.01)

(58) Field of Classification Search
CPC .............. A61N 7/02; A61N 2007/0052; A61N 2007/0082; A61N 2007/0056; A61N 7/022
See application file for complete search history.

(56) References Cited

U.S. PATENT DOCUMENTS

2007/0167773 A1  7/2007  Jeong et al.
2009/0326372 A1*  12/2009  Darlington .............. A61B 8/14
                                                           600/439
(Continued)

FOREIGN PATENT DOCUMENTS

JP    2001070333 A  *  3/2001
KR    10-0875208 B1     12/2008
(Continued)

OTHER PUBLICATIONS

Korean Office Action issued on Aug. 17, 2022 in corresponding Korean Patent Application No. 10-2021-0175227. (7 pages in Korean and 7 pages in English).
(Continued)

*Primary Examiner* — Baisakhi Roy
*Assistant Examiner* — Kaitlyn E Sebastian
(74) *Attorney, Agent, or Firm* — NSIP Law (57) ABSTRACT

The focused ultrasound device according to an embodiment comprises: an ultrasound probe structure including a treatment transducer for transmitting a focused ultrasound signal and an image transducer for transmitting and receiving an ultrasonic image signal; a reception switch for selecting a plurality of first elements among elements of the image transducer as protection areas and deactivating same, and selecting a plurality of second other elements among the elements of the image transducer as reception areas and activating same; an image beamformer for forming a reception beam signal by focusing ultrasonic echo signals received from the plurality of second elements; an image generation unit for generating an image for a target area in an object on the basis of the reception beam signal; and a control unit for controlling the selection of the protection areas and reception areas by means of a reception switch.

12 Claims, 10 Drawing Sheets

(56) References Cited

U.S. PATENT DOCUMENTS

| | | | |
|---|---|---|---|
| 2011/0144544 A1 | 6/2011 | Fan et al. | |
| 2013/0150715 A1* | 6/2013 | Lacoste | A61B 8/4483 600/439 |
| 2014/0114193 A1* | 4/2014 | Anthony | A61B 8/429 600/459 |
| 2014/0316269 A1 | 10/2014 | Zhang et al. | |
| 2016/0100822 A1* | 4/2016 | Kim | A61B 8/14 600/472 |
| 2019/0184204 A1 | 6/2019 | Ramamurthy | |
| 2019/0365347 A1* | 12/2019 | Abe | A61B 5/0095 |

FOREIGN PATENT DOCUMENTS

| | | | |
|---|---|---|---|
| KR | 10-1160958 B1 | 6/2012 | |
| KR | 10-2013-0016038 A | 2/2013 | |
| KR | 10-2014-0107852 A | 9/2014 | |
| KR | 10-1457666 B1 | 11/2014 | |
| KR | 10-2016-0041516 A | 4/2016 | |
| KR | 10-1625646 B1 | 5/2016 | |
| KR | 10-2019-0043378 A | 4/2019 | |
| WO | WO 2014/081108 A1 | 5/2014 | |
| WO | WO-2014193013 A1 * | 12/2014 | A61B 8/546 |

OTHER PUBLICATIONS

Korean Decision to Grant a Patent issued on Dec. 23, 2022 in corresponding Korean Patent Application No. 10-2021-0175227. (2 pages in Korean and 2 pages in English).

Office Action Issued Aug. 17, 2022 in counterpart Korean Patent Application KR 10-2021-0175227 (7 Pages in Korean).

Notice of Allowance Issued Dec. 23, 2022 in Counterpart Korean Patent Application KR 10-2021-0175227 (7 Pages in Korean).

Song, Junho, et al. "Large Improvement of the Electrical Impedance of Imaging and High-Intensity Focused Ultrasound (HIFU) Phased Arrays Using Multilayer Piezoelectric Ceramics Coupled in Lateral Mode." IEEE transactions on ultrasonics, ferroelectrics, and frequency control 59.7 (2012): 1584-1595.

Extended European search report issued on Jun. 26, 2024, in counterpart European Patent Application No. 22904570.3 (10 pages).

* cited by examiner

FOCUSED ULTRASOUND DEVICE AND IMAGE TRANSDUCER PROTECTION METHOD

CROSS REFERENCE TO RELATED APPLICATIONS

This application is a U.S. National Stage Application of International Application No. PCT/KR2022/019445, filed on Dec. 2, 2022, which claims the benefit under 35 USC 119(a) and 365(b) of Korean Patent Application No. 10-2021-0175227, filed on Dec. 8, 2021 in the Korean Intellectual Property Office, the entire disclosure of which is incorporated herein by reference for all purposes.

TECHNICAL FIELD

The present invention relates to diagnosis and treatment technology using ultrasound, and more particularly, to image scanning and treatment technology using focused ultrasound (FUS) for Image guided treatment.

The present invention is derived from research carried out as part of a study conducted as part of Collaborative Life-Cycle Medical Device R&D Project of the Ministry of Science and Information & Communication Technology, the Ministry of Trade, Industry, and Energy, the Ministry of Health and Welfare, and the Ministry of Food and Drug Safety [Project number: 9991006682, KMDF_PR_20200901_0009, research project name: Development of Commercialization of Market-Leading Ultrasound Image-Guide, High-Intensity Focused Ultrasound Treatment Device for Integrated Therapy for Pancreatic Cancer, research management institution: Korea Medical Device Development Fund, contribution rate: 100%, research supervising institute: IMGT. Co., Ltd., research period: Mar. 1, 2022-Dec. 31, 2022].

BACKGROUND ART

Ultrasound signals may be used in the treatment of biological tissues, such as cancer, tumors, lesions, and the like. Treatment with ultrasound is a method of treating a lesion by emitting ultrasound signals to the lesion of the human body. Ultrasound treatment may cause less trauma of a patient, compared to general surgical treatment or chemotherapy, and realize non-invasive treatment. Examples of the application of ultrasound treatment include liver cancer, bone sarcoma, breast cancer, pancreatic cancer, kidney cancer, soft tissue tumors, pelvic tumors, and the like.

DISCLOSURE

Technical Problem

According to an embodiment, a focused ultrasound device capable of protecting an image transducer from a therapeutic focused ultrasound (FUS) signal and removing image artifact and an image transducer protection method are proposed.

Technical Solution

A focused ultrasound device according to an embodiment includes: an ultrasound probe structure including a treatment transducer for transmitting a focused ultrasound signal and an image transducer for transmitting and receiving an ultrasonic image signal, a reception switch for selecting a plurality of first elements among elements of the image transducer as a protection area and deactivating the same, and selecting a plurality of second other elements among the elements of the image transducer as a reception area and activating the same, an image beamformer for forming a reception beam signal by focusing ultrasonic echo signals received from the plurality of second elements, an image generation unit for generating an image for a target area in an object on the basis of the reception beam signal, and a control unit for controlling the selection of the protection area and reception area by means of a reception switch.

The plurality of first elements may be in a central area of the image transducer in which the focused ultrasound signal reflected from an interface of the ultrasound probe structure to the image transducer is concentrated and the plurality of second elements may be in a peripheral area of the image transducer.

The protection area may include N elements located at the center of the entire scan lines, and the reception areas may include (the total number of channels−N)/2 elements on each of the left and right sides with respect to a center position of the entire scan lines.

The focused ultrasound device may further include a control unit configured to select the reception area by means of the reception switch on the basis of the image generated by the image generation unit.

The control unit may select and combine at least one from four methods including a first method of activating (the total number of channels−N)/2 elements on each of the left and right sides with respect to the center position of the entire scan lines, a second method of activating (the total number of channels−N)/2 elements on each of the left and right sides with respect to the center position of the entire scan lines and controlling a focusing angle, a third method of activating the total number of channels/2 elements on each of the left and right sides with respect to the center position of the entire scan lines, or a fourth method of activating the total number of channels/2 elements on each of the left and right sides with respect to the center position of the entire scan lines and controlling a focusing angle.

The image transducer may include a protective film configured to protect the protection area of the image transducer, the protective film may include any one of a diffuse reflection material, a reflective material, and an attenuating material, the diffuse reflection material or the reflective material may be any one of a copper foil, an aluminum foil, and a reflective plate made of plastic, and the attenuating material may be any one of natural rubber, latex, and silicone rubber.

The ultrasound probe structure may further include a column-shaped case and a membrane filled with an ultrasonic transmission medium along the shape of the case.

The ultrasound probe structure may further include a height adjustment unit configured to adjust a height of the case of the ultrasound probe structure. The height adjustment unit may adjust the height to satisfy $H'=L \cos \theta - D$, where $L$ denotes a FUS signal length of the outermost channel of the treatment transducer to the target area of the object, $H$ denotes a vertical distance from the treatment transducer to the target area of the object, $\theta$ denotes an angle between $L$ and $H$, $D$ denotes a vertical distance from the target area of the object to a skin surface of the object, and $H'$ denotes the height of the case of the ultrasound probe structure.

The ultrasound probe structure may further include a plurality of contact sensors configured to detect contact between the ultrasound probe structure and the target object.

The focused ultrasound device may further include a noise filter configured to filter noise from signals generated from each of the contact sensors, a contact switch configured to select a predetermined contact signal from among a plurality of contact signals from which the noise has been filtered, a signal processing unit configured to perform signal processing on the selected contact signal, and a control unit configured to determine a contact state at each position from the contact signal received from the signal processing unit and control the treatment transducer to transmit a FUS signal on the basis of the contact state.

The focused ultrasound device may further include an output unit configured to output a contact state and a contact instruction message to the outside.

Advantageous Effects

According to a focused ultrasound device and an image transducer protection method in accordance with an embodiment, an image transducer may be protected from a therapeutic focused ultrasound (FUS) signal, thereby minimizing damage to the image transducer and image artifact may be removed.

MODES OF THE INVENTION

The advantages and features of the present invention and the manner of achieving the advantages and features will become apparent with reference to embodiments described in detail below together with the accompanying drawings. However, the present invention may be implemented in many different forms and should not be construed as being limited to the embodiments set forth herein, and the embodiments are provided such that this disclosure will be thorough and complete and will fully convey the scope of the present invention to those skilled in the art, and the present invention is defined only by the scope of the appended claims. The same reference numerals refer to the same components throughout this disclosure.

In the following description of the embodiments of the present invention, if a detailed description of related known functions or configurations is determined to unnecessarily obscure the gist of the present invention, the detailed description thereof will be omitted herein. The terms described below are defined in consideration of the functions in the embodiments of the present invention, and these terms may be varied according to the intent or custom of a user or an operator. Therefore, the definitions of the terms used herein should follow contexts disclosed herein.

Hereinafter, embodiments of the present invention will be described in detail with reference to the accompanying drawings. However, the present invention may be realized in various forms, and the scope of the present invention is not limited to such embodiments. The embodiments of the present invention are provided to aid those skilled in the art in the explanation and the understanding of the present invention.

Figure 1:
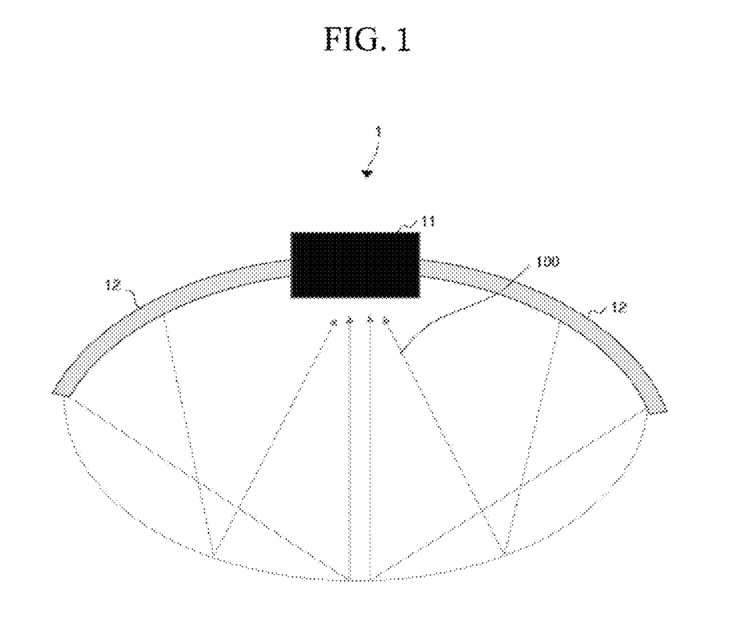
FIG. 1 is a diagram for explaining a principle in which an image transducer is damaged by a focused ultrasound (FUS) signal in a FUS device according to an embodiment of the present invention.

FIG. 1 is a diagram for explaining a principle in which an image transducer is damaged by a focused ultrasound (FUS) signal in a FUS device according to an embodiment of the present invention.

Referring to FIG. 1, a FUS device 1 includes an image transducer 11 and a treatment transducer 12. The structure of the image transducer 11 and the treatment transducer 12 may vary. For example, as shown in FIG. 1, the treatment transducer 12 may be formed around the image transducer 11 and the image transducer 11 may be formed in the center of the treatment transducer 12. However, the structure of the image transducer 11 and the treatment transducer 12 is not limited to this, and may be modified in various ways.

The image transducer 11 transmits an image ultrasound signal and an image ultrasonic echo signal reflected from a target area of an object. The FUS device 1 generates an image of the target area using the received ultrasonic echo signal, and uses the generated image to monitor the state of the object.

The treatment transducer 12 generates a thermal lesion by focusing a therapeutic FUS signal to the target area of the object and performs FUS treatment. The location of the target area may be identified through monitoring of the image transducer 11.

When the FUS signal transmitted through the treatment transducer 12 is reflected at the interface of an ultrasonic transmission medium (e.g., water) and a reflected FUS signal 100 is directed to the image transducer 11, the image transducer 11 may be thermally/mechanically damaged. As a result, an image obtained through the image transducer may have artifacts and thus reduced quality, which may cause a problem in diagnosis. The present invention proposes a technique for minimizing thermal/mechanical damage to and protecting the image transducer 11 from the FUS signal 100 reflected from the image transducer 11 among the FUS signals transmitted from the treatment transducer 12.

Figure 2:
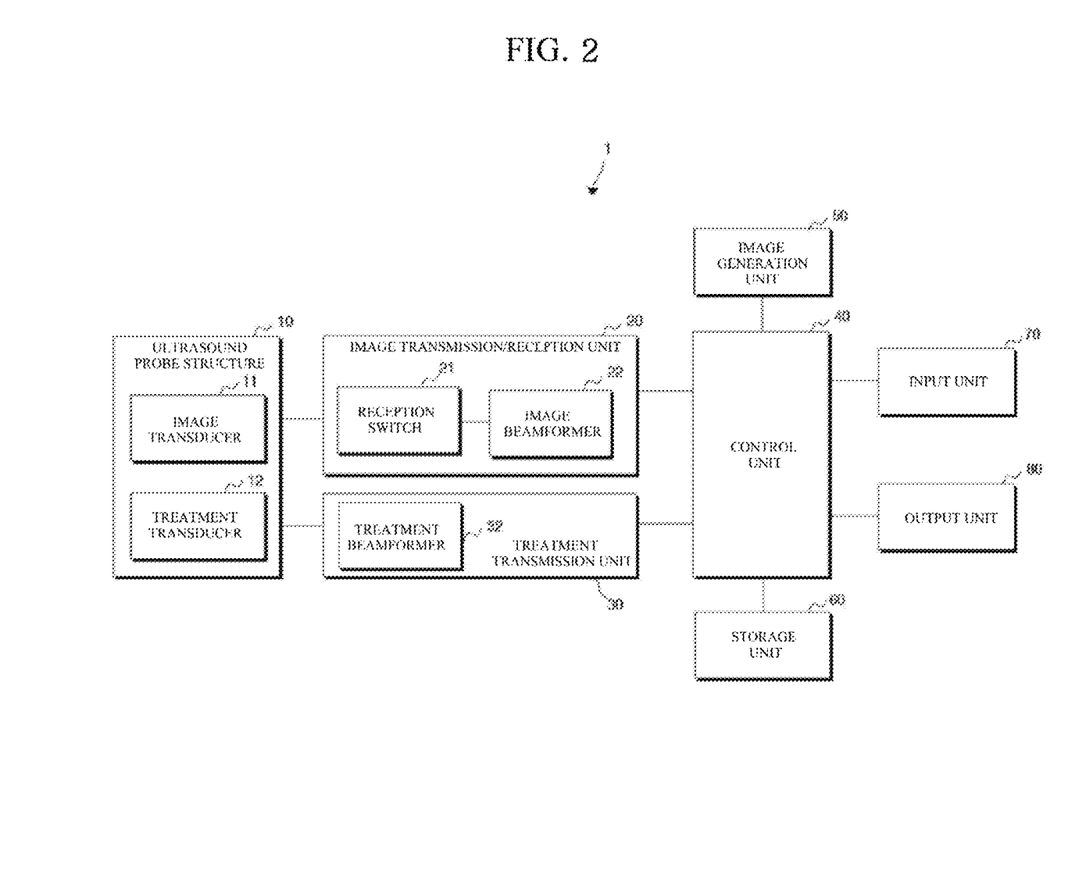
FIG. 2 is a diagram illustrating the configuration of a FUS device according to an embodiment of the present invention.

FIG. 2 is a diagram illustrating the configuration of a FUS device according to an embodiment of the present invention.

Referring to FIG. 2, a FUS device 1 includes an ultrasound probe structure 10, an image transmission/reception unit 20, a treatment transmission unit 30, a control unit 40, an image generation unit 50, a storage unit 60, an input unit 70, and an output unit 80.

The ultrasound probe structure 10 includes an ultrasound probe configured to transmit an ultrasound signal to the object, receive an ultrasonic echo signal from the object, and convert the received ultrasonic echo signal into an electrical signal. The ultrasound probe is a combination of the image transducer 11 and the treatment transducer 12.

A transducer array is provided at an end of the ultrasound probe. The transducer array refers to a plurality of elements arranged in an array. The transducer array generates an ultrasound signal while vibrating by an applied pulse signal or alternating current. The generated ultrasound signal is transmitted to the target area inside the object. The ultrasound signal generated by the transducer array is reflected from the target area inside the object, returning to the transducer array. The transducer array receives an ultrasonic echo signal reflected and returning from the target area and converts the received ultrasonic echo signal into an electrical signal. Each element in the transducer array may transmit and receive the ultrasound signal through each channel. The number of channels may be the same as the number of elements constituting the transducer array. Each element may include a piezoelectric vibrator or a thin film.

The ultrasound probe structure 10 may include a column-shaped case and a membrane filled with an ultrasonic transmission medium along the shape of the case so that the FUS signal is not reflected to the image transducer 11. An embodiment of this will be described below with reference to FIG. 6.

The image transmission/reception unit 20 includes a reception switch 21 and an image beamformer 22.

The reception switch 21 selects a plurality of first elements among elements constituting the image transducer 11 as a protection area and deactivates the same, and selects a plurality of second elements as a reception area and activates the same. The protection area is an area of the image transducer 11 expected to be thermally/mechanically damaged by the FUS signal. The plurality of first elements may be in the central area of the image transducer 11, and the plurality of second elements may be in the peripheral area of the image transducer 11. For example, when the image transducer 11 has a 1D transducer array structure, the protection area includes N elements located at the center of the entire scan line, and the reception area includes (the total number of channels–N)/2 elements on each of the left and right sides with respect to a center position of the entire scan lines. The protection area of the image transducer 11 corresponds to the central part, where the FUS signal reflected from the interface of the ultrasonic transmission medium of the ultrasound probe structure 10 to the image transducer 11 is concentrated. The control unit 40 may intentionally deactivate the second elements of the protection area selected by means of the reception switch 21 to block the reception of the FUS signal reflected to the image transducer 11, thereby protecting the second elements from the FUS signal and increasing the resolution of an ultrasound image.

The image beamformer 22 generates a transmission beam signal in response to a control signal of the control unit 40 and transmits the same to the image transducer 11, and when receiving an ultrasonic echo signal from the image transducer 11, generates a reception beam signal and transmits the same to the control unit 40. The image beamformer 22 may generates the reception beam signal by focusing the ultrasonic echo signals received from the plurality of second elements of the image transducer.

The treatment transmission unit 30 includes a treatment beamformer 32. The treatment beamformer 32 generates a FUS signal toward the target area of the object in response to the control signal of the control unit 40, and transmits the same to the treatment transducer 12.

The control unit 40 controls the overall operation of the FUS device 1. In particular, the control unit 40 calculates a delay profile for the plurality of elements constituting the image transducer 11, and calculates a time delay value according to the distance difference between the plurality of elements and a focal point of the object, on the basis of the calculated delay profile. In addition, the control unit 40 accordingly controls the image beamformer 22 to generate transmission/reception beam signals, and controls the treatment beamformer 32 to generate a FUS signal. The control unit 40 may generate a control command for each component of the FUS device 1 and control the FUS device 1, in response to an instruction or command of a user input through the input unit 70.

The control unit 40 may select the reception area by means of the reception switch 21 on the basis of the image generated by the image generation unit 50. An embodiment of this will be described below with reference to FIG. 4.

The control unit 40 may determine a contact state between the ultrasound probe structure 10 and the object from contact signals detected from a plurality of contact sensors, and control the treatment transducer 12 to transmit the FUS signal on the basis of the contact state. An embodiment of this will be described below with reference to FIGS. 6 and 9.

The image generation unit 50 generates an ultrasound image of the target area inside the object on the basis of the reception beam signal focused through the image transmission/reception unit 20.

The storage unit 60 temporarily or non-temporarily stores the ultrasound image generated by the image generation unit 50.

The input unit 70 is provided for the user to input a command for an operation of the FUS device 1. The user may input or set a diagnosis mode selection command, such as an ultrasound diagnosis start command, amplitude mode (A-mode), brightness mode (B-mode), color mode, Doppler mode (D-mode), and motion mode (M-mode), region of interest (ROI) setting information including the size and location of an ROI, and the like through the input unit 70.

The output unit 80 displays menus or information required for ultrasound diagnosis and ultrasound images obtained in the process of ultrasound diagnosis. The output unit 80 displays the ultrasound image of the target area inside the object generated by the image generation unit 50. The ultrasound image displayed on the output unit 80 may be an A-mode ultrasound image, a B-mode ultrasound image, or a three-dimensional (3D) stereoscopic ultrasound image. The output unit 80 may output a contact state between the ultrasound probe structure 10 and the object and a contact instruction message to the outside.

Figure 3:
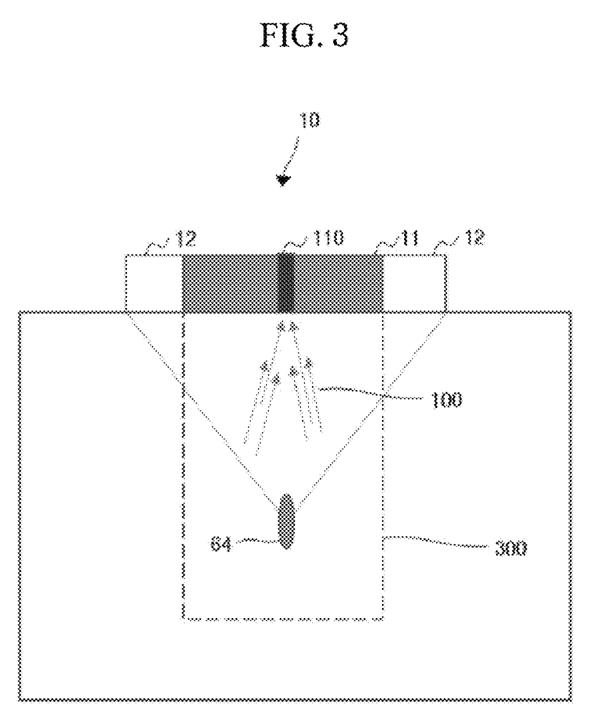
FIG. 3 is a view illustrating a protection area located in the center of an image transducer according to an embodiment of the present invention.

FIG. 3 is a view illustrating a protection area located in the center of an image transducer according to an embodiment of the present invention.

Referring to FIGS. 2 and 3, when the treatment transducer 12 focuses an FUS signal to the target area 64 of the object, part of the FUS signal 100 is reflected from the interface of the ultrasound probe structure 10 and concentrated at the center of the image transducer 11. Thus, the FUS device 1 sets the central part of the image transducer 11 as the protection area 110. Reference numeral 300 denotes an image range of the image transducer 11.

Figure 4:
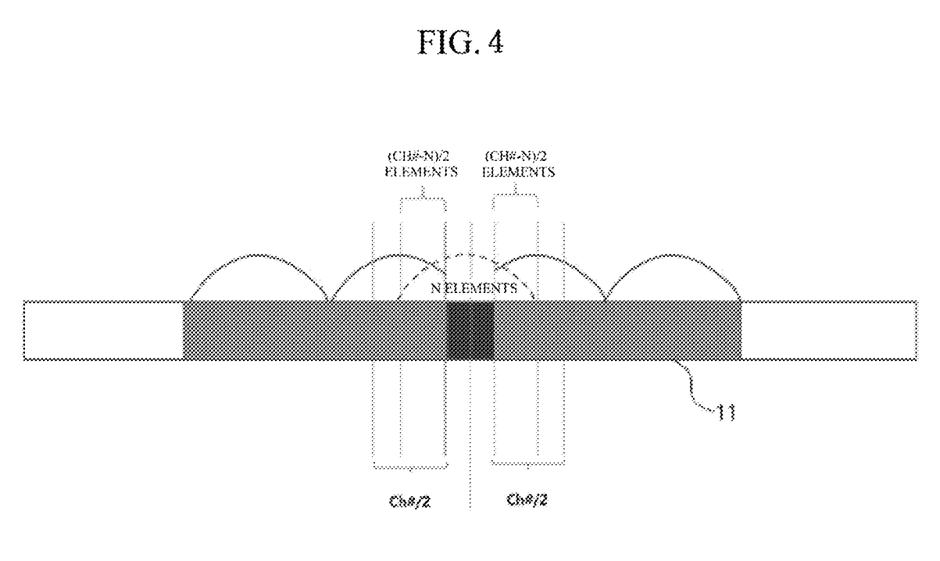
FIG. 4 is a view illustrating an example of channel activation for protecting a protection area on an entire scan line of an image transducer according to an embodiment of the present invention.

FIG. 4 is a view illustrating an example of channel activation for protecting a protection area on an entire scan line of an image transducer according to an embodiment of the present invention.

Referring to FIGS. 2 and 4, a transducer array is composed of a plurality of elements. In order to obtain an ultrasound image, a plurality of scan lines are required, and the FUS device 1 may perform beamforming of the focal point from the first scan line to the last scan line. The FUS device 1 transmits an ultrasound signal for each scan line, and generates an ultrasound image by receiving an ultrasonic echo signal reflected and returning from the target area of the object.

The FUS device 1 according to an embodiment may intentionally deactivate a predetermined scan line and activate only a predetermined scan line, rather than receiving ultrasound echo signals for all scan lines.

More specifically, the control unit 40 may select the reception area by means of the reception switch on the basis of the image generated by the image generation unit 50, and control a focusing angle of the reception beam signal. For example, when the image transducer 11 has a 1D transducer array structure, the control unit 40 may select and combine at least one from four methods. The four methods include a first method of activating (Ch #−N)/2 elements on each of the left and right sides with respect to the center position of the entire scan lines, a second method of activating (Ch #−N)/2 elements on each of the left and right sides with respect to the center position of the entire scan lines and controlling a focusing angle, a third method of activating Ch #/2 elements on each of the left and right sides with respect to the center position of the entire scan lines, and a fourth method of activating Ch #/2 elements on each of the left and right sides with respect to the center position of the entire scan lines and controlling a focusing angle. Here, Ch #represents the total number of channels.

When the image transducer 11 is damaged by an FUS signal, the resolution of the central part of an ultrasound image deteriorates. The control unit 40 may check the resolution of the ultrasound image generated by the image generation unit 50 to determine whether the image transducer 11 is damaged. In this case, when it is determined that the image transducer 11 is damaged based on the deteriorated resolution, the control unit 40 may control the reception switch 21 to select the first method of activating (Ch #−N)/2 elements on each of the left and right sides with respect to the center position of the entire scan lines. Further, the second method of controlling a focusing angle of the reception beam signal may be additionally combined to increase the resolution of the ultrasound image. For example, the control unit 40 may perform spatial compound for focusing the reception beam at different angles, rather than focusing the reception beam in a linear direction. In this case, image noise may be reduced, achieving good contrast and resolution.

Figure 5:
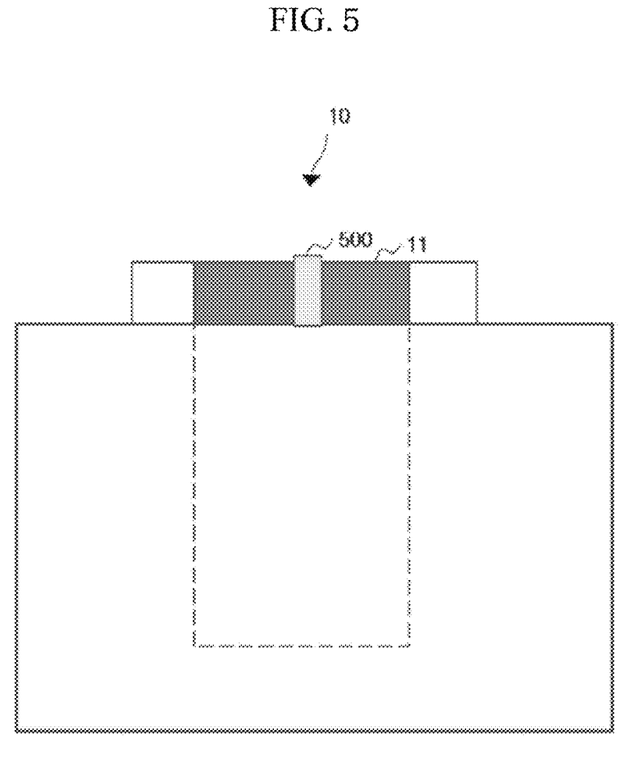
FIG. 5 is a view illustrating a FUS device for protecting a protection area of an image transducer using a protective film according to an embodiment of the present invention.

FIG. 5 is a view illustrating a FUS device for protecting a protection area of an image transducer using a protective film according to an embodiment of the present invention.

Referring to FIGS. 2 and 5, the ultrasound probe structure 10 includes a protective film 500 mounted on the protection area of the image transducer 11, causing the direction of the FUS signal to move away from the protection area of the image transducer 11. The protective film 500 may include any one of a diffuse reflection material, a reflective material, and an attenuating material.

The diffuse reflection material/reflective material may be, for example, a copper foil made of metal, an aluminum foil, a reflective plate such as an acrylic plate made of plastic, or the like. The thickness and material of the diffuse reflection material/reflective material may be selected to reduce the magnitude of the FUS signal incident to the image transducer to a predetermined value (e.g., −10 dB). However, if the thickness of the diffuse reflection material/reflective material is too thick, it affects the ultrasound signal of the adjacent image channel and the FUS signal of the treatment transducer, and hence, the thickness is limited within the allowable range. In this case, as the diffuse reflection material/reflective material, a material with a difference in impedance from the ultrasonic transmission medium (e.g., water) greater than a predetermined value may be used.

The attenuating material may be, for example, natural rubber, latex, silicone rubber, or the like such that it has a small difference in acoustic impedance from the ultrasonic transmission medium (e.g., water) and can attenuate ultrasound energy. The thickness and substance of the attenuating material may be selected in the same way as for the reflective material.

Figure 6:
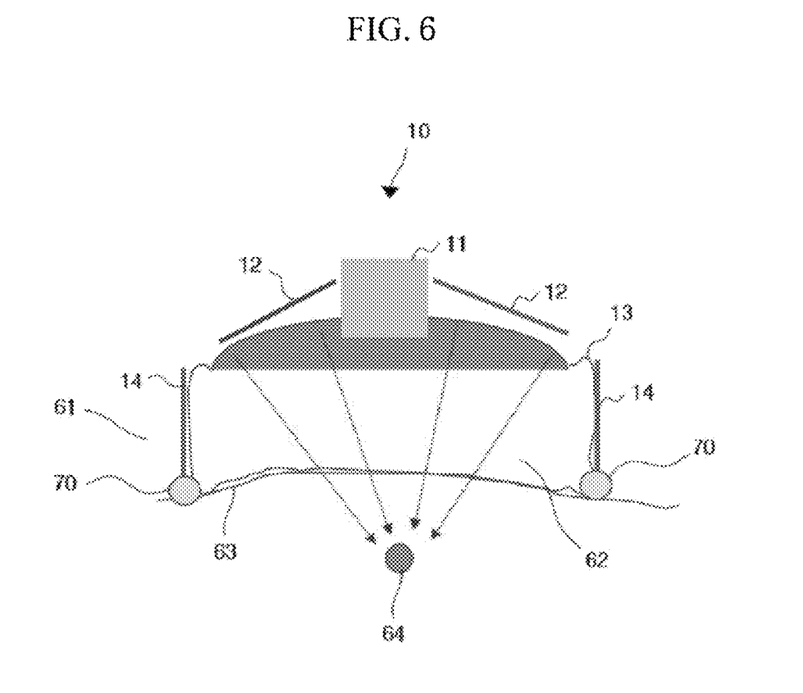
FIG. 6 is a view illustrating an ultrasound probe structure for protecting an image transducer according to an embodiment of the present invention.

FIG. 6 is a view illustrating an ultrasound probe structure for protecting an image transducer according to an embodiment of the present invention.

Referring to FIGS. 2 and 6, the ultrasound probe structure 10 may include a column-shaped case 14 and a membrane 13 filled with an ultrasonic transmission medium along the shape of the case 14. The case 14 is formed in a vertical direction with respect to a skin surface 63 of the object so that a FUS signal is not reflected. The case 14 may be in the form of a sound-absorbing plate.

The membrane 13 has a structure mounted inside the case 14 to block an ultrasound radiation surface. An accommodation space 62 is formed between a focused ultrasound radiation surface and the membrane 13 for accommodating the ultrasonic transmission medium, and the membrane 13 is made of an elastic material. In general, when the accommodation space 62 is filled with a set amount of ultrasonic transmission medium, the membrane 13 forms a hemispherical shape that is convex downward by an elastic force. In this case, the FUS signal may not reach the target area 64 of the object but may be reflected in an air layer 61 between the membrane 13 and the skin surface 63 of the object along the hemispherical shape of the membrane 13, and directed toward an intermediate element of the image transducer 11. In this case, the image transducer 11 may degrade.

In the FUS device 1 according to an embodiment, the case 14 of the ultrasound probe structure 10 is provided in the shape of a vertical column with respect to the skin surface 63 of the object so that the membrane 13 does not form a hemispherical shape when the accommodation space 62 is filled with the ultrasonic transmission medium. When the accommodation space 62 is filled with a set amount of the ultrasonic transmission medium, the membrane 13 tightly fits along the vertical shape of the case 62. Accordingly, the membrane 13 is formed in the shape of a column, rather than in the shape of a hemisphere, through the column-shaped case 14, so that the direction of the FUS signal is not formed in the air layer 61 outside the case 14, but in the target area 64 of the object. The height of the case 14 is adjustable. An embodiment of this will be described below with reference to FIG. 10.

The ultrasound probe structure 10 according to an embodiment includes a plurality of contact sensors 70. The plurality of contact sensors 70 detect whether the ultrasound probe structure 10 is in contact with the object. The plurality of contact sensors 70 may be formed along the periphery of the lower surface of the ultrasound probe structure 10 in contact with the object.

In order to prevent the air layer 60 from being generated due to lifting occurring when the ultrasound probe structure 10 is in contact with the object, the FUS device 1 detects the contact with the object using the plurality of contact sensors 70. The FUS device 1 determines the contact state at each position from contact signals detected by means of the plurality of contact sensors 70, and controls the treatment transducer to transmit a FUS signal on the basis of the contact states. In this case, the FUS device 1 blocks the transmission of the FUS signal of the treatment transducer in the case of incomplete contact, and transmits the FUS signal through the treatment transducer only in the case of complete contact. For example, contact signals are detected from a predetermined number or more of the plurality of contact sensors 70, the FUS device 1 determines that the ultrasound probe structure 10 is in contact with the skin surface of the object, and at this time, transmits the FUS signal through the treatment transducer. A device configuration for this will be described below with reference to FIG. 9.

Figure 7:
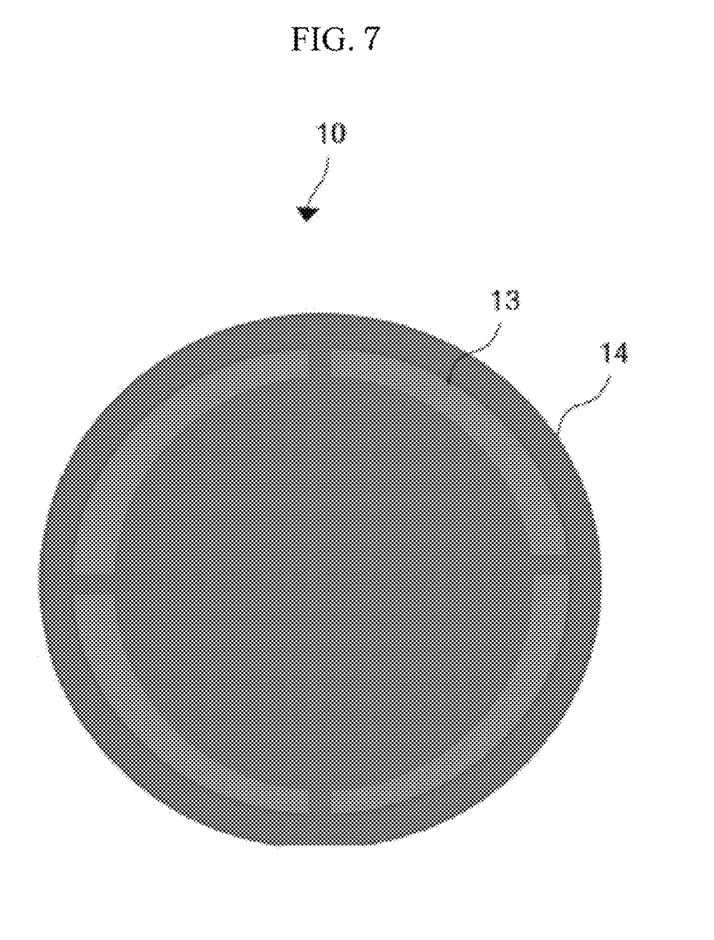
FIG. 7 is a top view of an ultrasound probe structure including a case and a membrane according to an embodiment of the present invention.

FIG. 7 is a top view of an ultrasound probe structure including a case and a membrane according to an embodiment of the present invention.

Referring to FIGS. 2 and 7, the ultrasound probe structure 10 includes a column-shaped case 14 and a membrane 13 filled with an ultrasonic transmission medium along the shape of the case 14, and may solve a problem in which a FUS signal is reflected to the image transducer 11 by the case 14.

Figure 8:
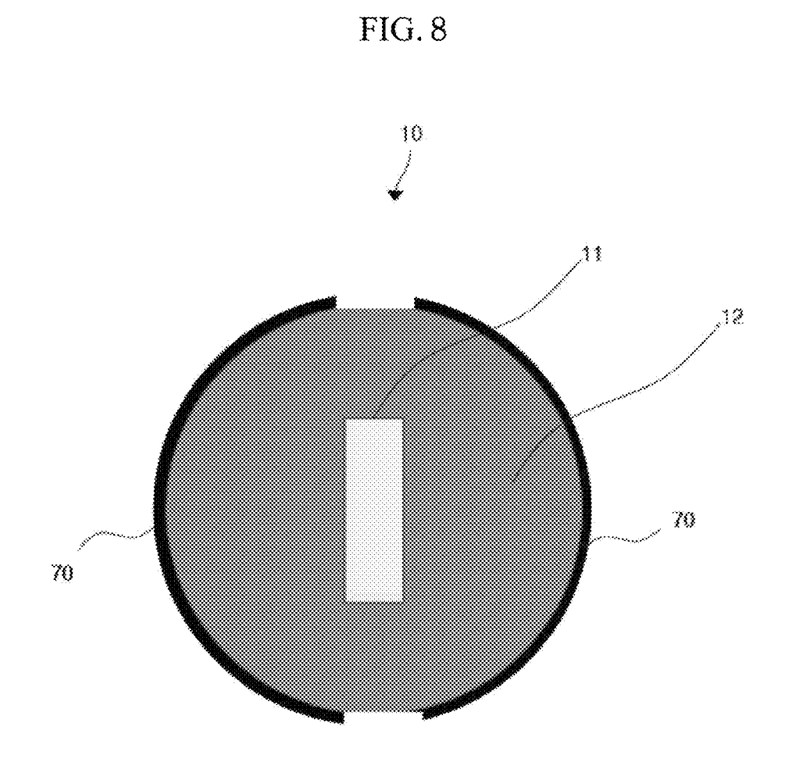
FIG. 8 is a bottom view of an ultrasonic probe structure including a plurality of contact sensors according to an embodiment of the present invention.

FIG. 8 is a bottom view of an ultrasonic probe structure including a plurality of contact sensors according to an embodiment of the present invention.

Referring to FIGS. 2 and 8, the ultrasound probe structure 10 includes a plurality of contact sensors 70. The FUS device 1 uses the plurality of contact sensors 70 to determine whether the ultrasound probe structure 10 is in contact with the object, and controls the treatment transducer 12 to transmit a FUS signal only in the case of contact with the object.

Figure 9:
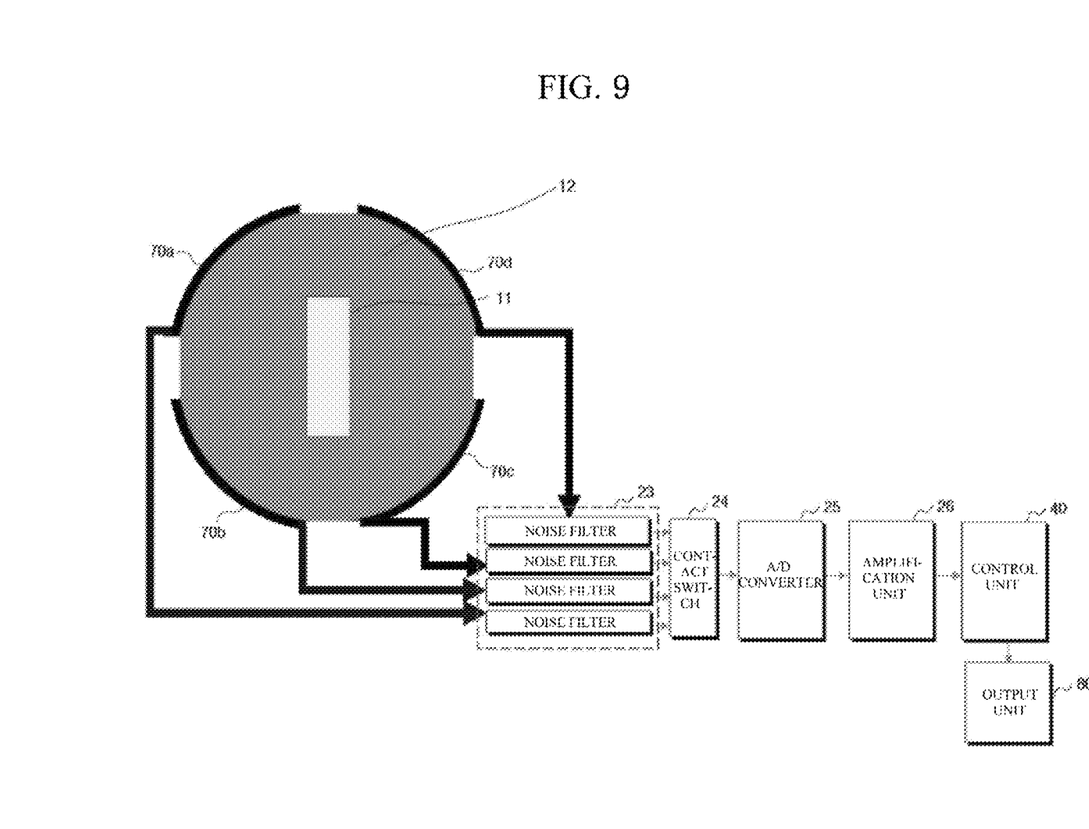
FIG. 9 is a diagram illustrating the configuration of a FUS device including a plurality of contact sensors according to an embodiment of the present invention.

FIG. 9 is a diagram illustrating the configuration of a FUS device including a plurality of contact sensors according to an embodiment of the present invention.

Referring to FIGS. 2 and 9, the FUS device 1 may include a plurality of contact sensors 70a, 70b, 70c, and 70d, a plurality of noise filters 23, a contact switch 24, a signal processing unit, a control unit 40, and an output unit 80. The signal processing unit may include an analog-to-digital (A/D) converter 25 and an amplification unit 26. The plurality of noise filters 23, the contact switch 24, and the signal processing unit may be located in the image transmission/reception unit 20 of FIG. 2.

The plurality of noise filters 23 filter noise by distinguishing a contact signal and a noise signal from signals generated from each of the contact sensors 70a, 70b, 70c, and 70d.

The contact switch 24 selects a predetermined contact signal from among a plurality of contact signals from which noise has been filtered by the plurality of noise filters 23 and transmits the selected contact signal to the A/D converter 25.

The signal processing unit performs signal processing on the contact signal. For example, the A/D converter 25 converts an analog signal into a digital signal, and the amplification unit 26 amplifies the digital signal.

The control unit 40 determines a contact state at each position from the contact signal received from the signal processing unit, and controls the treatment transducer 12 to transmit the FUS signal on the basis of the contact state. For example, as shown in FIG. 9, when the control unit 40 detects contact signals from three or more (contact rate of 75%) among the four contact sensors 70a, 70b, 70c, and 70d, the control unit 40 determines that the ultrasound probe structure 10 is in contact with the skin surface of the object, and at this time, controls the treatment transducer 12 to transmit the FUS signal. Further, when all four contact sensors 70a, 70b, 70c, and 70d detect contact, the control unit 40 may determine complete contact (contact rate of 100%), and control the treatment transducer 12 to transmit the FUS signal only in the case of complete contact.

The control unit 40 outputs the contact state to the outside through the output unit 80 when the contact state satisfies a predetermined condition. At this time, a contact instruction message may be output through the output unit 80 together. For example, a contact instruction message may be output through a light-emitting diode (LED), voice, screen, or the like.

Figure 10:
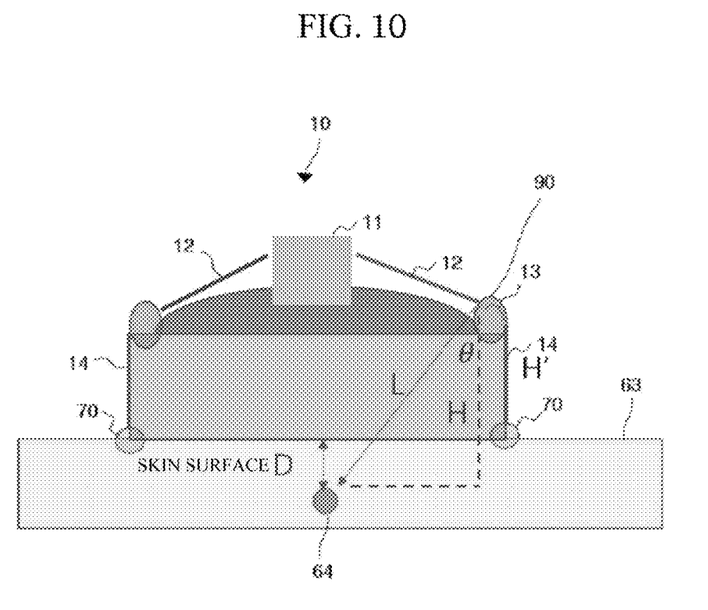
FIG. 10 is a view illustrating an example of adjusting the height of a case of an ultrasound probe structure according to an embodiment of the present invention.

FIG. 10 is a view illustrating an example of adjusting the height of a case of an ultrasound probe structure according to an embodiment of the present invention.

Referring to FIGS. 2 and 10, a height adjustment unit of the FUS device 1 adjusts the height H' of the case 14 of the ultrasound probe structure 10 to $L \cos \theta - D$. Here, L denotes a FUS signal length of the outermost channel of the treatment transducer 12 to the target area 64 of the object, H denotes a vertical distance from the treatment transducer 12 to the target area 64 of the object, $\theta$ denotes an angle between L and H, D denotes a vertical distance from the target area 64 of the object to the skin surface 63 of the object, and H' denotes the height of the case 14 of the ultrasound probe structure 10.

When the accommodation space at the lower end of the membrane 13 is completely filled with the ultrasonic transmission medium, the ultrasonic transmission medium slightly overflows to the top of the membrane 13, as shown by reference numeral 90, so that the FUS device 1 may adjust the amount of ultrasonic transmission medium supplied.

Heretofore, the present invention has been described by focusing on the exemplary embodiments. It can be understood by those skilled in the art to which the present invention pertains that the present invention can be implemented in modified forms without departing from the essential feature of the present invention. Therefore, the disclosed embodiments should be considered as illustrative rather than determinative. The scope of the present invention is defined by the appended claims rather than by the foregoing description, and all differences within the scope of equivalents thereof should be construed as being included in the present invention.

The invention claimed is:

1. A focused ultrasound device comprising:
   an ultrasound probe structure comprising a treatment transducer for transmitting a focused ultrasound signal and an image transducer for transmitting and receiving an ultrasonic image signal;
   a reception switch for selecting a plurality of first elements among elements of the image transducer as a protection area and deactivating same, and selecting a plurality of second other elements among the elements of the image transducer as a reception area and activating same;
   an image beamformer for forming a reception beam signal by focusing ultrasonic echo signals received from the plurality of second elements;

an image generator for generating an image for a target area in an object on the basis of the reception beam signal; and a controller for controlling the selection of the protection area and reception area by means of a reception switch, to protect the image transducer from the focused ultrasound signal of the treatment transducer, wherein the plurality of first elements are in a central area of the image transducer the plurality of second elements are in a peripheral area corresponding on each of the left and right sides of the central area of the image transducer.

2. The focused ultrasound device of claim 1, wherein the central area of the image transducer is an area where the focused ultrasound signal is reflected from the interface of the ultrasound probe structure and concentrated at the image transducer when the treatment transducer focuses the focused ultrasound signal to the target area of the object.

3. The focused ultrasound device of claim 1, wherein the protection area comprises N elements located at the center of entire scan lines, and the reception area comprises (the total number of channels−N)/2 elements on each of the left and right sides with respect to a center position of the entire scan lines.

4. The focused ultrasound device of claim 1, wherein the controller is configured to select the reception area by means of the reception switch on the basis of the image generated by the image generator.

5. The focused ultrasound device of claim 4, wherein the controller is configured to select from four methods including a first method of activating (the total number of channels−N)/2 elements on each of the left and right sides with respect to a center position of entire scan lines, a second method of activating (the total number of channels−N)/2 elements on each of the left and right sides with respect to the center position of the entire scan lines and controlling a focusing angle, a third method of activating the total number of channels/2 elements on each of the left and right sides with respect to the center position of the entire scan lines, or a fourth method of activating the total number of channels/2 elements on each of the left and right sides with respect to the center position of the entire scan lines and controlling a focusing angle.

6. The focused ultrasound device of claim 1, wherein the image transducer comprises a protective film configured to protect the protection area of the image transducer, the protective film comprises any one of a diffuse reflection material, a reflective material, and an attenuating material, the diffuse reflection material or the reflective material is any one of a copper foil, an aluminum foil, and a reflective plate made of plastic, and the attenuating material is any one of natural rubber, latex, and silicone rubber.

7. The focused ultrasound device of claim 1, wherein the ultrasound probe structure further comprises a column-shaped case and a membrane filled with an ultrasonic transmission medium along the shape of the case.

8. The focused ultrasound device of claim 7, wherein the ultrasound probe structure further comprises a height adjustment actuator configured to adjust a height of the case of the ultrasound probe structure.

9. The focused ultrasound device of claim 8, wherein the height adjustment actuator is configured to adjust the height to satisfy $H'=L \cos \theta - D$, where L denotes a FUS (Focused Ultrasound) signal length of the outermost channel of the treatment transducer to the target area of the object, H denotes a vertical distance from the treatment transducer to the target area of the object, $\theta$ denotes an angle between L and H, D denotes a vertical distance from the target area of the object to a skin surface of the object, and H' denotes the height of the case of the ultrasound probe structure.

10. The focused ultrasound device of claim 1, wherein the ultrasound probe structure further comprises a plurality of contact sensors configured to detect contact between the ultrasound probe structure and the target object.

11. The focused ultrasound device of claim 10, further comprising:

a noise filter configured to filter noise from signals generated from each of the contact sensors;

a contact switch configured to select a predetermined contact signal from among a plurality of contact signals from which the noise has been filtered;

a signal processor configured to perform signal processing on the selected contact signal; and a controller configured to determine a contact state at each position from the contact signal received from the signal processor and control the treatment transducer to transmit a FUS signal on the basis of the contact state.

12. The focused ultrasound device of claim 10, further comprising a display configured to output a contact state and a contact instruction message to the outside.

* * * * *